United States Patent [19]

Spruill

[11] Patent Number: 5,545,122
[45] Date of Patent: Aug. 13, 1996

[54] INFLATABLE SPECULUM

[76] Inventor: Theresa Spruill, 326 N. Broadway, Nyack, N.Y. 10960

[21] Appl. No.: 320,958

[22] Filed: Oct. 12, 1994

[51] Int. Cl.$^6$ ...................................... A61B 1/32
[52] U.S. Cl. .................. 600/222; 600/186; 600/195; 600/203; 600/207; 604/98; 604/104; 606/193
[58] Field of Search .................. 600/186, 195, 600/203, 206, 207, 210, 220, 222, 226; 604/98, 104; 606/193

[56] References Cited

U.S. PATENT DOCUMENTS

| 896,505 | 8/1908 | Ament | 604/104 |
|---|---|---|---|
| 3,332,414 | 7/1967 | Gasper | 600/222 |
| 3,575,163 | 4/1971 | Gasper | 600/222 |
| 3,720,199 | 3/1973 | Rishton et al. | 604/98 |
| 3,841,317 | 10/1974 | Awais | 600/203 |
| 3,900,033 | 8/1975 | Leininger et al. | 606/193 |
| 4,884,559 | 6/1989 | Collins | 128/17 |
| 5,007,409 | 4/1991 | Pope | 600/220 |
| 5,072,720 | 12/1991 | Francis et al. | 600/220 |
| 5,179,937 | 1/1993 | Lee | 600/220 |
| 5,231,973 | 8/1993 | Dickie | 600/222 |
| 5,236,437 | 8/1993 | Wilk et al. | 606/207 |
| 5,250,074 | 10/1993 | Wilk et al. | 606/207 |
| 5,329,937 | 7/1994 | Krstevich et al. | 600/186 |

Primary Examiner—Richard J. Apley
Assistant Examiner—Kelly McGlashen
Attorney, Agent, or Firm—Notaro & Michalos

[57] ABSTRACT

A speculum comprises a pair of elongated blades having elongated hollow bills therein. Each bill is at least partly covered by a flexible expandable bladder. One or more ports communicate between the interior of each bill and the interior of the bladder. Gas lines are connected to each bill for supplying compressed gas to a valve to each bill to expand each bladder. A second valve can be activated for deflating each bladder. For use, the speculum blades are inserted into a body cavity and the bladders inflated to gently expand the body cavity. Blades can then be moved apart to perform an examination. When the examination is completed, the blades are moved toward each other and the bladders are deflated before the blades are withdrawn from the body cavity.

11 Claims, 1 Drawing Sheet

INFLATABLE SPECULUM

FIELD AND BACKGROUND OF THE INVENTION

The present invention relates, in general, to surgical instruments, and in particular, to a new and useful speculum which has inflatable blades to reduce the discomfort associated with the use of the instrument.

Specula are currently available in plastic and metal varieties. Gynecological patients who are examined using a speculum report pain and discomfort. Further, a speculum having metal blades tends to be cold, further adding to the patient's discomfort. Patients having small or narrow vaginas, pediatric and elderly patients, cancer patients and patients undergoing various treatments such as irradiation, are even more susceptible to the discomfort and pain associated with the use of a speculum.

The discomfort caused by a cold speculum has been addressed in U.S. Pat. No. 3,841,317 which teaches the use of a heat insulating pocket over the blades of a speculum for reducing the discomfort associated with heat transfer between the speculum and the patient. Also see U.S. Pat. No. 5,007,409 which teaches the use of soft resilient silicone rubber blade sheaths for the blades of a speculum.

Other references which show various constructions for a speculum include U.S. Pat. No. 4,597,382 and U.S. Pat. No. 5,072,720.

The use of inflatable tubes and bladders is also noted in the field of medicine but not in the field of speculum construction.

See U.S. Pat. No. 3,782,370 for the disclosure of an inflatable surgical retractor and U.S. Pat. No. 3,168,092 for the disclosure of an inflatable medical probe. U.S. Pat. No. 681,387 (issued in 1901) discloses a squeeze bulb for use in conjunction with a speculum, for dispensing medication while the speculum is in use, but not as part of a speculum.

A need remains for improvements in the construction of the speculum, in particular to reduce pain and discomfort associated with its use.

SUMMARY OF THE INVENTION

The present invention comprises a speculum having inflatable blades or bills which can be inflated once the bills are in position in the vagina. Before they are inflated, the bills are extremely thin to facilitate insertion without discomfort. The blades or bills are also made of plastic and are at least partly wrapped by a flexible bladder which is inflatable. No metal parts come into contact with the patient, reducing discomfort associated with a cold spatulum specifically or any type of heat transfer in general.

By inflating the blades only after insertion, the patient's tissues are expanded more gently and with less pain. To facilitate examination, the blades are pivotally mounted to each other so that they can be spread. Since the spreading force is applied against the walls of the vagina through the soft inflated bladders, even the normally uncomfortable expansion process is made less painful.

Accordingly, an object of the present invention is to provide a speculum comprising upper and lower elongated blades, means for movably mounting the upper and lower blades to each other with each blade including a rigid bill and a flexible bladder at least partly covering the rigid bill, and inflation means connected to each blade for inflating each bladder.

A further object of the present invention is to provide a speculum where each bill is hollow and has at least one port communicating between an interior of the bill and an interior of the flexible bladder for inflating the bladder through the bill of each blade.

A still further object of the present invention is to provide means for deflating each bladder after it has been inflated.

A still further object of the present invention is to provide a speculum which is comfortable to use, simple in design and rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
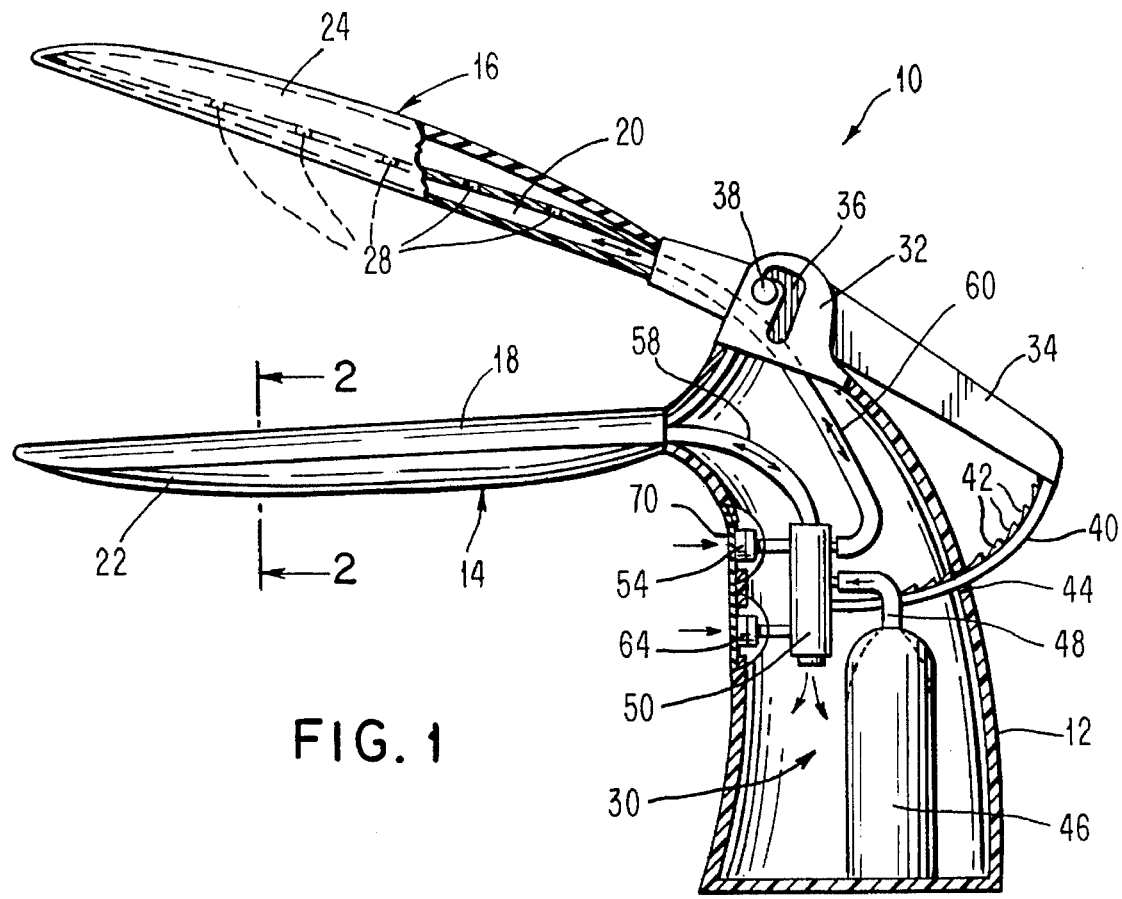
FIG. 1 is a side-elevational view, partly in section of a speculum according to the present invention.
Figure 2:
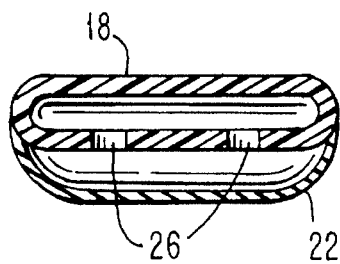
FIG. 2 is a sectional view taken along line 2—2 of FIG. 1.

Referring to the drawings in particular, the invention embodied in FIGS. 1 and 2 comprises a speculum generally designated 10 having a handle 12 to which a lower blade generally designated 14 is rigidly connected. An upper blade 16 is pivotly mounted to handle 12 so that the blades 14, 16 can be moved toward and away from each other during an examination using the speculum.

Lower blade 14 comprises a hollow rigid lower bill 18 whose cross-sectional shape is shown in FIG. 2. Upper blade 16 comprises an upper hollow rigid bill 20 having a similar but inverted sectional shape. Each of the rigid hollow bills 18, 20 are at least partly covered by elastic bladders 22, 24. As shown in FIG. 2, bladder 22 covers only the lower half of lower bill 18. Bladder 24 covers only the upper half of upper bill 20. The present invention includes the possibility of utilizing inflatable bladders that completely envelop the upper and lower bills or, conversely, cover less than an entire bottom or top surface of a respective bill.

In the embodiment illustrated, each of the bills contain a plurality of gas ports at 26 (not shown in FIG. 1) for lower blade 14 and at 28 for upper blade 16, which communicate between the interior of each hollow bill and the interior of each bladder covering that bill. Gas is forced to pass from the interior of a respective bill into the interior of a respective bladder in order to inflate the bladder as the bladder contracts. Gas passes from the bladder back into the respective bill, for through ports 26, 28 when the bladder is deflated.

Inflation/deflation means generally designated 30 are positioned within handle 12. Advantageously, handle 12 is hollow and made of plastic as are bills 18 and 20.

To movably mount the upper blade 16 to the lower bill 14, the upper blade 16 includes an extension 34 extending behind upper blade 16 and between a pair of flat plastic ears 32 extending upwardly from handle 12 (only one ear visible in FIG. 1). J-shaped openings 36 extend through each of the ears and receive a cylindrical trunnion or pivot pin 38 of blade 16. Blade 16 can rotate on handle 12 by rotation of pins 38 in their respective J-shaped openings 36 to move the inner surfaces of bills 18 and 20 toward and away from each other. When the pivot pins 38 are in the short portion of the J-shaped openings 36 as shown in FIG. 1, bills 18 and 20 are distanced from each other. Pivot pins 38 can be moved along the J-shaped openings 36 to the inferior limit of the long leg of the J, placing the blades but at closer proximity to each other.

To hold the blades in any desired pivotable position with respect to each other, a curved projection 40, having inner locking teeth 42, extends downwardly and inwardly from the lower end of extension 34, and into an aperture 44 on the back of handle 12. The position of aperture 44 and the shape of projection 40 are selected so that the teeth 42 are resilient pressed against the upper edge of the aperture 44 locking the upper blade 16 in any position into which it is moved by pressing extension 34 downwardly against handle 12. This position can be released by exerting slight downward pressure on projection 40, releasing locking teeth 42 from the aperture 44.

Figure 3:
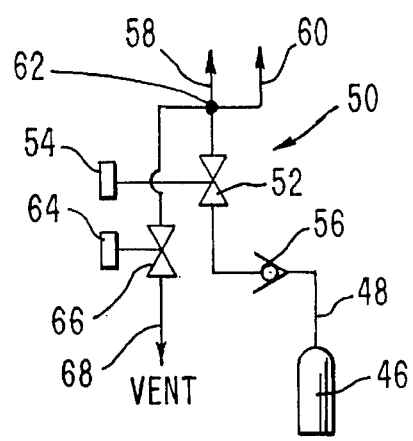
FIG. 3 is a schematic diagram illustrating a gas circuit for inflating and deflating the bladders of the present invention.

The inflation/deflation means 30 comprises a source of compressed gas such as a compressed gas cylinder 46 which may contain any appropriate compressed gas such as $CO_2$ or nitrous oxide. The pressurized gas is supplied over a gas line or viaduct 48 to a gas manifold 50 containing two valves for respectively inflating and deflating both bladders simultaneously. As best shown in FIG. 3, manifold 50 contains an inflation valve 52 which is normally closed but can be opened by pressing a push-button 54. This allows the passage of compressed gas along gas line 48, across a check valve 56 and through valve 52. From valve 52, gas is carried to a pair of additional gas lines or viaducts 58 and 60 which are connected at a junction 62. As shown in FIG. 1, line 60 is connected between manifold 50 and the interior of rigid hollow bill 20 while line 58 is connected between manifold 50 and the interior of hollow rigid bill 18.

When push-button 54 is released, valve 52 is closed, for example, through the action of a spring (not shown). This maintains the pressure in the now inflated bladders 22, 24.

When the physician wishes to deflate the bladders, a second push-button 64 is pressed, opening a deflation valve 66 and venting compressed gas from the junction 62 through valve 66 to a vent 68 as shown in FIG. 3.

Returning to FIG. 1, each of the push-buttons 54, 64, are covered by flexible waterproof covers 70, with push-buttons being pushable by the flexibility of the covers. This helps close off the interior of handle 12 making the instrument easier to clean after use.

In use, the physician first manipulates the handle and upper blade 16 so that the blades are close to each other. With the bladders in their collapsed or deflated conditions, the bills are inserted into the vagina and then the physician carefully depresses inflation push-button 54 to inflate bladders 22 and 24 to a desired extent. Once the appropriate amount of inflation is achieved, push-button 54 is released. The physician can then pivot blade 16 away from blade 14 and conduct an examination. When the examination is complete, the blades are pivoted back toward each other and push-button 64 is pressed to deflate and collapse the elastic bladders 22, 24. This makes it easier to withdraw the blades of the speculum.

Any appropriate, rigid, easily cleaned plastic can be used for the handle and rigid portions of the blade while any appropriate flexible elastic and expandable synthetic or natural rubber or elastomer can used for the bladders 22, 24. Although shown partly inflated, the bladders rest closely against the bills when they are deflated. The parts of the handle and blades which are rigid can also be made of metal although this is less desirable.

Although two rows of ports 26 and 28 can be used on the outer surface of each of the rigid hollow bills 18 and 20, as few as one port can be used, or one row of ports or multiple rows of ports. Alternatively, the gas lines 58 and 60 can be connected directly to the bladders. In this case, the bills need not be hollow but need only be rigid to maintain a basic shape for each blade while minimizing the cross-sectional area of each bill.

Although a compressed gas cylinder 46 has been shown as the source of compressed gas, other sources of compressed gas can be used such as a squeeze bulb, a larger compressor connected to the handle of the speculum, or any other known source of compressed gas.

While a specific embodiment of the invention has been shown and described in detail to illustrate the application of the principles of the invention, it will be understood that the invention may be embodied otherwise without departing from such principles.

What is claimed is:

1. A speculum for examining a vagina comprising:

upper and lower elongated blades for insertion into the vagina;

means for movably mounting the upper and lower blades to each other;

each blade including a rigid bill with an outer surface for facing a wall of the vagina when the blades are inserted, and a flexible bladder at least partly covering the outer surface of said rigid bill;

each bill being hollow and including at least one port communicating between an interior of the bill and an interior of the bladder; and inflation means connected to each bill for inflating each bladder so that each inflated bladder pushes outwardly against walls of the vagina when the blades are inserted and the bladders are inflated.

2. A speculum according to claim 1, wherein said inflation means comprises a valve said valve connected to each blade for supplying a compressed gas to each bladder to inflate each bladder, and a source of compressed gas connected to the valve, the valve comprising an inflation valve which is activatable to pass the compressed gas to each bladder.

3. A speculum according to claim 2, including a deflation valve said deflation valve connected to each bladder and a vent connected to the deflation valve, the deflation valve being activatable to vent gas from each bladder to deflate each bladder after each bladder has been inflated.

4. A speculum according to claim 3, wherein the source of compressed gas comprises a compressed gas cylinder.

5. A speculum according to claim 1, wherein said means for movably mounting comprises a handle fixed to one of said blades, the other of said blades being pivotably mounted to said handle.

6. A speculum according to claim 5, wherein said inflation means comprises a valve said valve connected to each blade for supplying a compressed gas to each bladder to inflate each bladder, and a source of compressed gas connected to the valve, the valve comprising an inflation valve which is activatable to pass the compressed gas to each bladder.

7. A speculum according to claim 6, including a deflation valve connected to each bladder and a vent connected to the deflation valve, the deflation valve being activatable to vent gas from each bladder to deflate each bladder after each bladder has been inflated.

8. A speculum according to claim 7, wherein the source of compressed gas comprises a compressed gas cylinder.

9. A speculum according to claim 5, wherein said handle includes a pair of ears each having a J-shaped opening therethrough, said blade which is pivotably mounted to said handle comprising an extension having a pair of pivot pins each engaged into one of said J-shaped openings.

10. A speculum according to claim 9, including an aperture in said handle and a projection extending from said extension, said projection extending into the aperture and being engageable in a plurality of positions in the aperture for adjusting a relative position between said blades.

11. A speculum according to claim 10, wherein said handle is hollow, said inflation means being positioned in said handle.

* * * * *